United States Patent
Aramata et al.

[11] Patent Number: 6,156,380
[45] Date of Patent: Dec. 5, 2000

[54] METHOD FOR PREPARING CONTACT MASS FOR ORGANOHALOSILANE SYNTHESIS

[75] Inventors: Mikio Aramata; Yoichi Tanifuji; Hisashi Konishi; Susumu Ueno; Tetsuya Inukai; Toshio Shinohara, all of Annaka, Japan

[73] Assignee: Shin-Etsu Chemical Co., Ltd., Tokyo, Japan

[21] Appl. No.: 09/412,567

[22] Filed: Oct. 5, 1999

[30] Foreign Application Priority Data

Oct. 5, 1998 [JP] Japan .................................. 10-297633

[51] Int. Cl.[7] ........................................................ B05D 7/00
[52] U.S. Cl. ............................. 427/217; 427/11; 427/212; 427/215; 427/216; 427/242
[58] Field of Search ............................. 427/11, 212, 215, 427/216, 217, 242, 256

[56] References Cited

U.S. PATENT DOCUMENTS

| 4,314,908 | 2/1982 | Downing et al. ........................ 252/182 |
| 4,390,510 | 6/1983 | Ritzer et al. ............................. 423/342 |
| 5,372,845 | 12/1994 | Rangaswamy et al. ................ 427/216 |

FOREIGN PATENT DOCUMENTS

| 2653700 | 5/1997 | Japan . |
| 9-235114 | 9/1997 | Japan . |

OTHER PUBLICATIONS

English Abstract for 3–44393.
English Abstract for 9–235114.

*Primary Examiner*—Shrive Beck
*Assistant Examiner*—Paul D. Strain
*Attorney, Agent, or Firm*—Millen, White, Zelano & Branigan

[57] ABSTRACT

A contact mass for use in the synthesis of organohalosilanes is prepared by adding metallic copper particles to metallic silicon particles, and rubbing the particles against each other under high shear forces in a non-oxidizing atmosphere, thereby forming a metallic copper thin film on the surface of the metallic silicon particles in a spot pattern or entirely. The contact mass is capable of reducing the time required for activation and has an extended lifetime.

15 Claims, 4 Drawing Sheets

SE IMAGE
(×500)

SE IMAGE (×500)

SiK$_\alpha$ IMAGE (←)

CuK$_\alpha$ IMAGE (↑)

METHOD FOR PREPARING CONTACT MASS FOR ORGANOHALOSILANE SYNTHESIS

This invention relates to a method for preparing a metallic silicon-copper contact mass for use in the synthesis of organohalosilanes.

BACKGROUND OF THE INVENTION

In the industry, the Rochow reaction is typically employed for the synthesis of organohalosilanes such as methylchlorosilanes. That is, reaction of alkyl halides and aryl halides such as methyl chloride and benzil chloride with metallic silicon particles is carried out at 250 to 500° C. in the presence of a copper catalyst and a minor amount of a co-catalyst. Although a variety of by-products usually form in this reaction in addition to the main products, the reaction conditions should be maintained to comply with the supply/demand balance of organochlorosilanes. In particular, this reaction requires to keep a high reaction rate, and a key technology in the synthesis of methylchlorosilanes is to increase the selectivity of the mostly demanded dichlorosilane and a key technology in the synthesis of phenylsilanes is to produce a silane composition matching with the demand.

Industrially, the synthesis of organohalosilanes is generally carried out in a reactor such as a fluidized bed or vibrating fluidized bed while feeding thereto a contact mass consisting of metallic silicon, a copper catalyst and optionally a co-catalyst. This process has many drawbacks including that a long time is taken for activation until the reaction reaches a steady state, the activity decreases with the progress of reaction, the reaction rate and selectivity decreases, the amount of unnecessary by-products such as high-boiling fractions increases, and the reactor and piping are clogged due to agglomeration of the catalyst and co-catalyst, which requires exchange of the contact mass and descaling and cleaning of the reactor. In particular, the conventional Rochow reaction requires a very long time for activation until the reaction reaches a steady state. The steady state, in turn, is relatively short and the yield decreases with the lapse of time. In the synthesis of methylchlorosilanes, for example, there arise problems that high-boiling fractions such as disilanes and undesired products such as trichlorosilane increase due to side-reaction and the exchange of the contact mass in the reactor becomes necessary.

Making investigations on these problems from various viewpoints, we have found that formation of Cu—Si active sites on the surface of metallic silicon follows a long process and hence, takes a long time, and copper continuously deposits on the surface of metallic silicon to form an inactive thick copper layer.

More particularly, in a common process, metallic silicon particles and a copper catalyst are mechanically mixed to prepare a contact mass with which a reactor is charged. After the contact mass is heated under an inert gas stream, methyl chloride is fed thereto to effect activation and reaction. Since the time taken for activation is long, it is naturally necessary to charge the system with a large excess of the copper catalyst and feed the additional contact mass in a high concentration. For this reason, as the reaction proceeds, copper thickly covers the surface of metallic silicon particles, which can reduce the reaction rate and deposition of carbon, and eventually an increase of by-products such as disilanes and a drop of selectivity. Since the active copper catalyst and co-catalyst are used in relatively large amounts, copper and the co-catalyst can be coagulated or the contact mass be bound with copper and the co-catalyst, which prevents effective utilization of copper and the co-catalyst and adversely affects the fluidized bed.

With respect to the contact masses for use in the Rochow reaction for synthesizing organohalosilanes, many improvements in the contact mass including the co-catalyst have been proposed from the composition viewpoint. With respect to the preparation of the contact mass, however, most prior art methods are to simply mix its components. There have been made few proposals for the preparation of a contact mass, based on the action mechanism of the catalyst and/or co-catalyst.

With respect to a contact mass consisting of metallic silicon and a copper catalyst and/or a co-catalyst, Japanese Patent No. 2653700 discloses a method for preparing trimethoxysilane by effecting gas phase reaction using a copper chloride-carrying metallic silicon contact mass. JP-A 9-235114 discloses the preparation of copper silicide-bearing metallic silicon particles. However, the Rochow reaction is reaction between solid phase silicon and gas phase organic halide, and the organohalosilane product volatilizes off from the reaction site as a gas. In the former patent, silicon at the center gradually decreases and the copper concentration and the copper film thickness relatively increase. As a result, the life becomes shortened and the co-catalyst fails to fully exert its effect, and the selectivity of silane is insufficient. In the latter patent, metallic silicon powder and a catalyst are simply mixed to form a contact mass, a reactor is charged therewith, an inert gas is passed through the contact mass to heat it to a reaction temperature (above 250° C.), and an alkyl halide is passed through the contact mass to effect reaction. Basically, this process is substantially the same as the current conventional processes. Even when copper silicide was previously formed as proposed therein, its effect was not found significant.

An object of the invention is to provide a method for preparing a contact mass for the synthesis of organohalosilanes, which contact mass can significantly reduce the time required for activation and even when added in a small amount, sustain reaction activity.

SUMMARY OF THE INVENTION

We have found that by adding metallic copper particles and optionally co-catalyst metal particles or co-catalyst metal-containing copper alloy particles to metallic silicon particles, introducing the mixture into a mixing or grinding machine capable of applying strong shear forces, known as a "space walk type mixer" or "mechanofusion mixer," and rubbing the particles against each other under high shear forces in a non-oxidizing atmosphere, a thin film of metallic copper or a mixture of metallic copper and co-catalyst metal or co-catalyst metal-containing copper alloy is formed on the surface of metallic silicon particles in a fine spot pattern or over the entire surface. When the resulting particles are used as a contact mass, the time required for activation can be significantly reduced. Even when effective Cu—Si active sites gradually decrease with the progress of reaction, the desired reaction activity can be sustained by adding only a small amount of the contact mass to compensate for the loss. The outstanding demands to shorten the activation time and prolong the contact mass lifetime are met in this way.

According to the invention, there is provided a method for preparing a contact mass for use in the synthesis of organohalosilanes, comprising the steps of adding metallic copper particles to metallic silicon particles, and rubbing the particles against each other under high shear forces in a non-oxidizing atmosphere, thereby forming a metallic copper thin film at least partially on the surface of the metallic silicon particles.

In another aspect, the invention provides a method for preparing a contact mass for use in the synthesis of organohalosilanes, comprising the steps of adding particles of a co-catalyst metal-containing copper alloy or a mixture of a co-catalyst metal-containing copper alloy or a co-catalyst metal and metallic copper to metallic silicon particles, and rubbing the particles against each other under high shear forces in a non-oxidizing atmosphere, thereby forming a thin film of the co-catalyst metal-containing copper alloy or the mixture of a co-catalyst metal-containing copper alloy or a co-catalyst metal and metallic copper at least partially on the surface of the metallic silicon particles.

DESCRIPTION OF THE PREFERRED EMBODIMENTS

Figure 1:
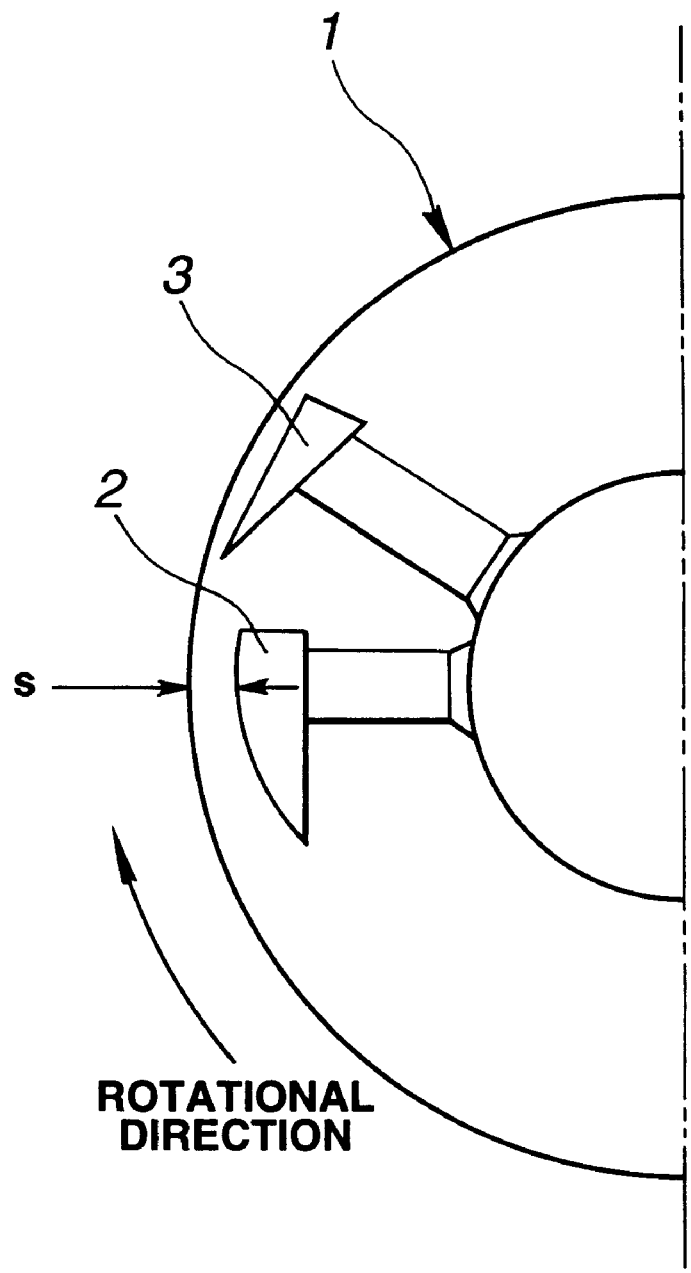
FIG. 1 schematically illustrates a mechanofusion apparatus.

In order to eliminate the drawbacks of the Rochow reaction of synthesizing organohalosilanes by reacting alkyl halides or aryl halides with metallic silicon particles in the presence of a copper catalyst, that is, to shorten the induction period or time taken for activation until reaction reaches a steady state, and to reduce a drop of contact mass activity and significantly prolong the lifetime of the contact mass effective for continuous operation, the invention makes a modification on the surface of metallic silicon by forming a thin layer and/or fine spots of copper catalyst on the surface of metallic silicon particles.

In the first step of the method according to the invention, particles of (1) metallic copper, (2) a co-catalyst metal-containing copper alloy, (3) a mixture of a co-catalyst metal-containing copper alloy and metallic copper or (4) a mixture of a co-catalyst metal and metallic copper (to be referred to as catalyst particles, hereinafter) are added to metallic silicon particles.

The metallic silicon particles used herein preferably have a mean particle size of about 10 μm to about 10 mm.

As the metallic copper, use may be made of stamped copper, electrolytic copper or atomized copper. The co-catalyst metal used herein may be any well-known one such as zinc or tin. Any stamped metal, electrolytic metal or atomized metal may also be used as the co-catalyst metal or copper alloy. These catalyst particles preferably have a mean particle size of up to about 2 mm, and especially about 10 to 200 μm.

Preferably the metallic copper is added in an amount of up to about 10 parts, more preferably about 0.1 to 10 parts, most preferably about 2 to 8 parts by weight, per 100 parts by weight of the metallic silicon.

An appropriate amount of the co-catalyst metal added is about 0.001 to 1 part, more preferably about 0.001 to 0.2 parts by weight, per 100 parts by weight of the metallic silicon.

After the catalyst particles are added to the metallic silicon particles, high shear forces are applied to the particles in a non-oxidizing atmosphere to rub the particles against each other, thereby forming a thin film of the catalyst on part or the entirety of the surface of the metallic silicon particles.

In the prior art, a copper catalyst and a co-catalyst are added to metallic silicon by mechanically mixing metallic silicon with particles or powders of the catalyst and co-catalyst in metal, alloy or compound form to produce a contact mass, which is subject to reaction. This process has several drawbacks. When copper is added in metallic form, a long time passes until the formation of a Cu—Si phase presenting active sites for reaction, and activation requires a long period of time. On the other hand, when copper chloride is added simply in powder or particulate form, activation can be achieved within a relatively short time, but the contact mass has a short lifetime. The present invention solves this problem by mixing and grinding metallic silicon particles with copper particles such as stamped copper powder, electrolytic copper or atomized copper in a non-oxidizing atmosphere and in a grinding/mixing device capable of applying strong shear forces, thereby forming a thin film of the catalyst metal on the surface of metallic silicon particles.

The metallic silicon particles and the catalyst particles are rubbed under high shear forces. As the grinding/mixing device capable of applying strong shear forces, use may be made of a so-called "mechanofusion" device, attritor, ball mill, or vertical roller mill.

Referring to FIG. 1, a mechanofusion device is schematically illustrated. The device includes a rotating casing 1 and a stationary support having inner pieces 2 and scrapers 3 mounted thereon (only one set of an inner piece and a scraper is shown). The scraper 3 is located downstream of the inner piece 2 with respect to the rotating direction of the casing 1. Raw material (metallic silicon particles and metallic copper particles) is admitted into the casing 1. The casing 1 is rotated to centrifugally push the raw material against the inner wall of the casing 1 and shear forces are applied to the raw material between the inner piece 2 and the casing 1 whereby the metallic silicon particles are modified at the surface. The raw material modified between the casing 1 inner wall and the inner piece 2 is scraped off by the scraper 3. In this way, the operation of applying shear forces to the raw material is repeated. It is noted that the casing 1 is cooled in order to avoid any abnormal temperature rise by frictional heat. Namely, the mechanofusion device has the rotating casing 1 and the stationary inner piece 2 which cooperate to apply compression, shear and grinding actions to powder particles. The scraper 3 serves to scrape off the powder compressed between the inner piece 2 and the casing 1. Under these actions, the mother particles and surface-covering particles premixed are strongly bound while generating heat. The device is capable of applying mechanical energy to particles of a single material or plural materials to achieve (1) surface fusion, (2) dispersion and mixing, and (3) particle size control.

It is understood that actual operation is carried out by monitoring the power to the motor and the temperature of the powder particles at the inner piece. The number of revolutions of the casing 1 and the clearance S between the casing 1 and the inner piece 2 are properly selected. It is preferred that the casing 1 is rotated at 300 to 3,000 rpm, and especially 800 to 2,200 rpm, and the clearance is set at 0.1 to 10 mm, and especially 0.5 to 5 mm.

The frictional grinding must be carried out in a non-oxidizing atmosphere, such as nitrogen gas, argon gas, hydrogen gas or a mixture thereof.

Although conventionally ground metallic silicon particles are surface covered with a thin oxide film which is detrimental to the desired reaction, the frictional grinding in a non-oxidizing atmosphere permits the catalyst metal (such as metallic copper) to act on the active silicon surface, effectively forming a catalyst metal-silicon phase, that is, an active contact mass.

In the thus obtained contact mass, a thin film (or microparticulates) of the catalyst is formed on the surface of metallic silicon particles entirely or in a fine speckled pattern. The thickness of the catalyst thin film is preferably from a monomolecular thickness to about 1 micron ($\mu$m) and more preferably from a monomolecular thickness to about 0.1 micron. The desired effect is also exerted with metallic silicon particles having attached thereto a catalyst thin film (or catalyst metal atomic layer) with a thickness corresponding to one to ten molecules.

The contact mass obtained by the method of the invention is useful in the Rochow reaction for synthesizing organohalosilanes from alkyl halides and metallic silicon particles while its use is the same as conventional contact masses.

The invention has several advantages. Since a thin catalyst-silicon layer capable of forming active sites for reaction is previously formed on the surface of metallic silicon by applying the mechanical alloying technique, the time required for activation is significantly reduced, and so the lifetime of the contact mass is prolonged. Although conventionally ground metallic silicon particles are surface covered with a thin oxide film which is detrimental to the desired reaction, the frictional grinding in a non-oxidizing atmosphere permits the metallic copper and co-catalyst to directly act on the active silicon surface, effectively forming active reaction sites, that is, an active contact mass.

EXAMPLE

Examples of the invention are given below by way of illustration and not by way of limitation.

Example 1

Figure 2:
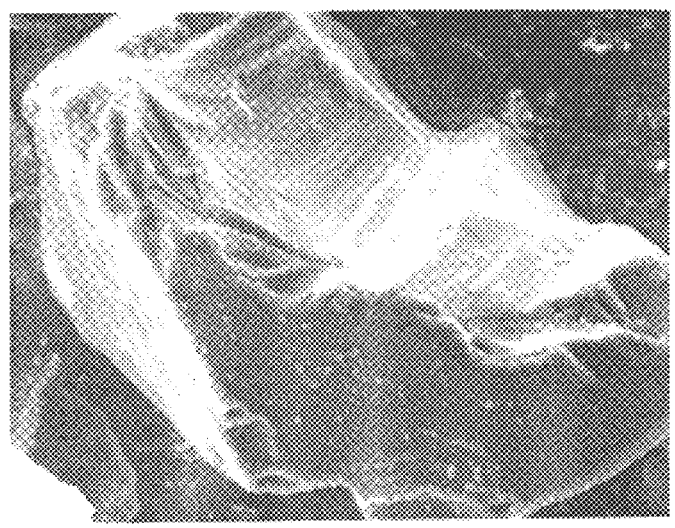
FIG. 2 illustrates the SEM views of the surface of the contact mass obtained in Example 1, FIG. 2A being an SE image of 500×, FIG. 2B being an EPMA image (SiKα image), and FIG. 2C being an EPMA image (CuKα image).
Figure 2:
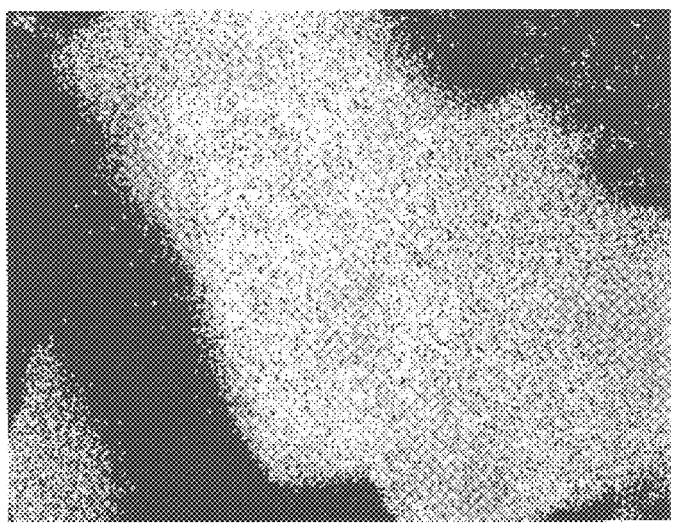
Figure 2:
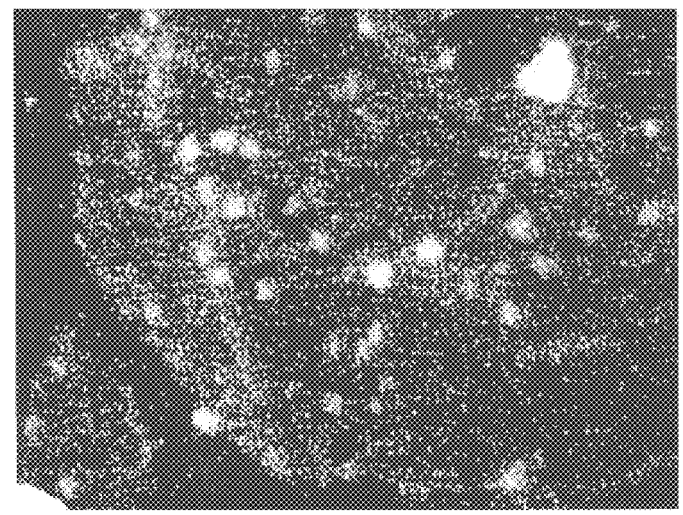
Figure 3:
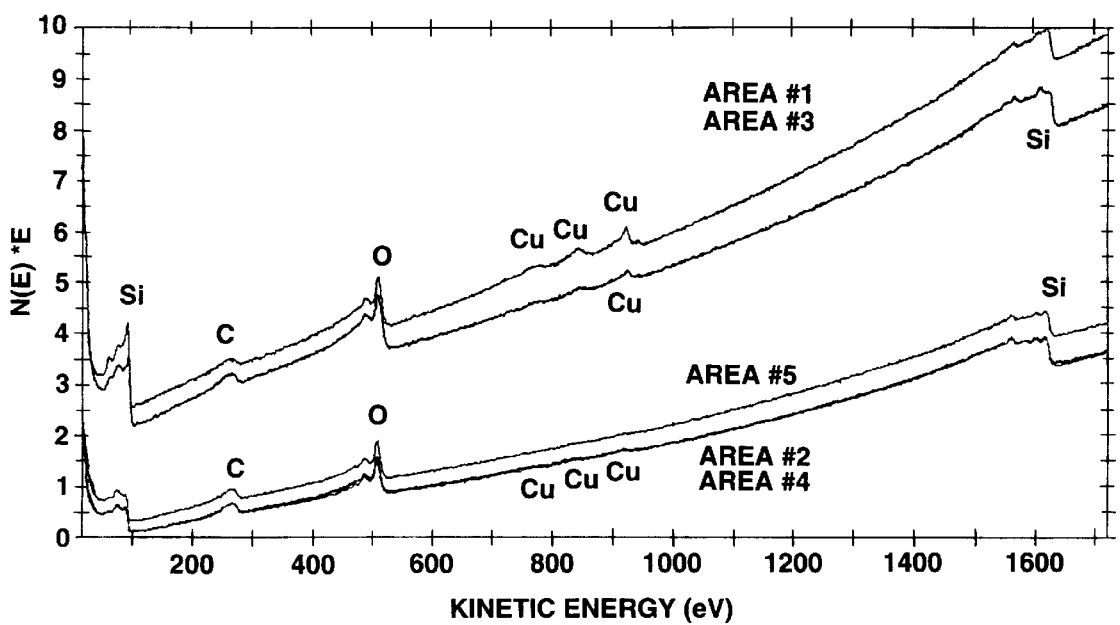
FIG. 3 illustrates a surface Auger spectrum of the contact mass in Example 1.
Figure 4:
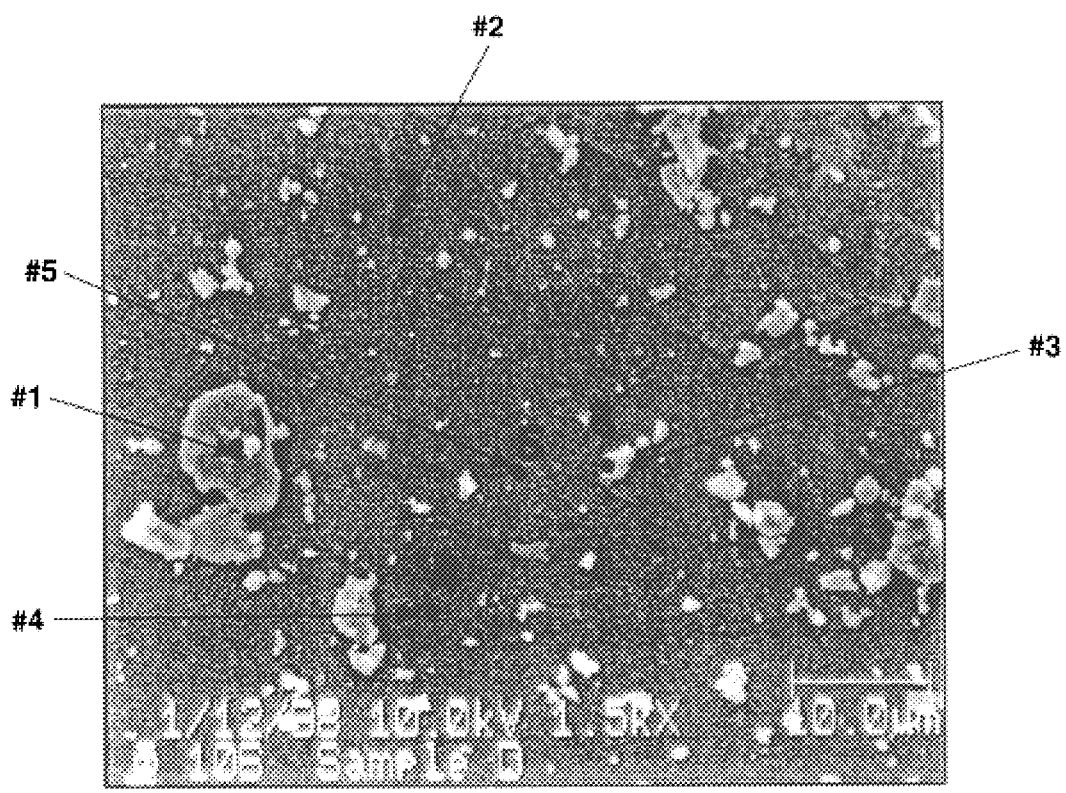
FIG. 4 is an image (1500×) of the contact mass in Example 1.

To metallic silicon particles having a mean particle size of about 80 $\mu$a was added 3.0% by weight of electrolytic copper powder. Using a "mechanofusion" device (Hosokawa Micron K.K.), the particles were uniformly agitated and ground in an argon stream at an agitation power of 15 kW and a casing revolution of 300 rpm. The surface of the thus ground particles were observed by x-ray microanalysis (electron probe microanalysis) and Auger spectroscopy. The results are shown in FIGS. 2, 3 and 4. FIG. 2A is an SE image of 500×, FIG. 2B is an EPMA image (SiK$\alpha$ image), and FIG. 2C is an EPMA image (CuK$\alpha$ image). FIG. 4 is an image (1,500×) of mechanofusion contact mass surface. FIG. 3 is a diagram showing Auger spectra at the mechanofusion contact mass surface, that is, Auger spectra at areas #1 to #5 in FIG. 4.

As seen from FIGS. 2 and 3, in the contact mass obtained by the mechanofusion treatment, copper element thinly covers the entire surface of metallic silicon. It is also observed that copper is attached in a spot pattern.

To 51.5 g of the copper-bearing metallic silicon particles, 0.1 g of zinc powder and 0.0025 g of tin powder were added, obtaining a contact mass. A reactor having an inner diameter of 5 cm and a height of 30 cm was charged with this contact mass while passing a gas mixture of methyl chloride and nitrogen therethrough. Reaction was carried out under conditions: a reaction temperature of 310° C., a reaction time of 10 hours, a reactor internal pressure of 1.2 kg/cm$^2$, and a gas flow rate of 1.0 Nl/min. The results are shown in Table 1.

Example 2

To metallic silicon particles having a mean particle size of about 80 pm was added 2.0% by weight of electrolytic copper powder. Using a "mechanofusion" device (Hosokawa Micron K.K.), the particles were uniformly agitated and ground in an argon stream at an agitation power of 15 kW and a casing revolution of 300 rpm.

To 51 g of the copper-bearing metallic silicon particles, 0.1 g of zinc powder and 0.005 g of tin powder were added, obtaining a contact mass. A reactor having an inner diameter of 5 cm and a height of 30 cm was charged with this contact mass while passing a gas mixture of methyl chloride and nitrogen therethrough. Reaction was carried out under the same conditions as in Example 1. The results are shown in Table 1.

Example 3

To 150 g of metallic silicon particles having a mean particle size of about 80 $\mu$m were added 4.5 g of electrolytic copper powder, 0.3 g of zinc powder and 0.0075 of tin powder. Using a "mechanofusion" device (Hosokawa Micron K.K.), the particles were uniformly agitated and ground in an argon stream at an agitation power of 15 kW and a casing revolution of 300 rpm.

A reactor having an inner diameter of 5 cm and a height of 30 cm was charged with 53 g of the resulting contact mass while passing a gas mixture of methyl chloride and nitrogen therethrough. Reaction was carried out under the same conditions as in Example 1. The results are shown in Table 1.

Example 4

To 150 g of metallic silicon particles having a mean particle size of about 80 $\mu$m were added 3.0 g of electrolytic copper powder, 0.3 g of zinc powder and 0.015 g of tin powder. Using a "mechanofusion" device (Hosokawa Micron K.K.), the particles were uniformly agitated and ground in an argon stream at an agitation power of 15 kW and a casing revolution of 300 rpm.

A reactor having an inner diameter of 5 cm and a height of 30 cm was charged with 51 g of the resulting contact mass while passing a gas mixture of methyl chloride and nitrogen therethrough. Reaction was carried out under the same conditions as in Example 1. The results are shown in Table 1.

Comparative Example

Metallic silicon particles, electrolytic copper powder, zinc powder, and tin powder were simply mixed in the same blending ratio as in Example 1. Using the resulting mixture as a contact mass, reaction was carried out under the same conditions as in Example 1. The results are shown in Table 1.

TABLE 1

| | Production rate (g silane/hr) | Si conversion (%) | Composition M (%) | T (%) | D (%) |
|---|---|---|---|---|---|
| E1 | 16.7 | 72.6 | 0.87 | 3.13 | 92.0 |
| E2 | 16.8 | 73.0 | 1.08 | 3.92 | 91.3 |
| E3 | 14.1 | 61.2 | 1.17 | 2.87 | 92.8 |
| E4 | 16.1 | 70.1 | 0.83 | 3.29 | 92.3 |
| CE | 5.2 | 22.4 | 2.02 | 5.49 | 87.7 |

M: $(CH_3)_3SiCl$
T: $CH_3SiCl_3$
D: $(CH_3)_2SiCl_2$

In the Rochow reaction of synthesizing organohalosilanes by reacting alkyl halides or aryl halides such as methyl chloride with metallic silicon in the presence of a copper catalyst and a co-catalyst, the prior art has the drawbacks that a very long activation time or induction period is required until the reaction rate or selectivity reaches a steady state, and the steady state is relatively short lasting, whereas the present invention solves these problems and produces a contact mass capable of reducing the time required for activation and having an extended lifetime.

Japanese Patent Application No. 10-297633 is incorporated herein by reference.

Reasonable modifications and variations are possible from the foregoing disclosure without departing from either the spirit or scope of the present invention as defined by the claims.

What is claimed is:

1. A method for preparing a contact mass for use in the synthesis of organohalosilanes, comprising:

admitting metallic copper particles an metallic silicon particles into a rotating casing of a mechanofusion device including said rotating casing and a stationary support having inner pieces and scrapers mounted thereon so that said scrapers are located downstream of said inner pieces with respect to the rotating direction of the casing, and rotating said casing to centrifugally push the metallic copper particles and the metallic silicon particles against the inner wall of said casing in a non-oxidizing atmosphere thereby applying high shear forces to the metallic copper particles and the metallic silicon particles between said inner pieces and said casing, whereby a metallic copper thin film is formed at least partially on the surface of the metallic silicon particles.

2. The method of claim 1 wherein the thin film is attached to the surface of the metallic silicon particles in a fine spot pattern.

3. The method of claim 1 wherein the metallic silicon particles have a mean particle size of 10 μm to 10 mm.

4. The method of claim 1 wherein up to 10 parts by weight of metallic copper is added per 100 parts by weight of the metallic silicon particles.

5. The method of claim 1 wherein the thin film has a thickness from a monomolecular thickness to no more than about 1 μm.

6. The method of claim 5 wherein the thin film has a thickness corresponding to 1 to 10 molecules.

7. The method of claim 1 wherein the non-oxidizing atmosphere is composed of nitrogen, argon, hydrogen or a mixture thereof.

8. A method for preparing a contact mass for use in the synthesis of organohalosilanes, comprising the steps of:

adding particles of a co-catalyst metal-containing copper alloy or a mixture of a co-catalyst metal-containing copper alloy or a co-catalyst metal and metallic copper to metallic silicon particles, and rubbing the particles against each other under high shear forces in a non-oxidizing atmosphere, thereby forming a thin film of the co-catalyst metal-containing copper alloy or the mixture of a co-catalyst metal-containing copper alloy or a co-catalyst metal and metallic copper at least partially on the surface of the metallic silicon particles.

9. The method of claim 8 wherein the thin film is attached to the surface of the metallic silicon particles in a fine spot pattern.

10. The method of claim 8 wherein the metallic silicon particles have a mean particle size of 10 μm to 10 mm.

11. The method of claim 8 wherein up to 10 parts by weight of metallic copper is added per 100 parts by weight of the metallic silicon particles.

12. The method of claim 8 wherein the thin film has a thickness from a monomolecular thickness to no more than about 1 μm.

13. The method of claim 12 wherein the thin film has a thickness corresponding to 1 to 10 molecules.

14. The method of claim 8 wherein the non-oxidizing atmosphere is composed of nitrogen, argon, hydrogen or a mixture thereof.

15. The method of claim 1 wherein the metallic copper particles are added in an amount of about 2 to about 8 parts by weight per 100 parts by weight of the metallic silicon particles.

* * * * *